US010165975B2

(12) United States Patent
Hyde et al.

(10) Patent No.: US 10,165,975 B2
(45) Date of Patent: Jan. 1, 2019

(54) PREGNANCY MONITORING DEVICES, SYSTEMS, AND RELATED METHODS

(71) Applicant: Elwha LLC, Bellevue, WA (US)

(72) Inventors: Roderick A. Hyde, Redmond, WA (US); Jordin T. Kare, San Jose, CA (US); Lowell L. Wood, Bellevue, WA (US)

(73) Assignee: ELWHA LLC, Bellevue, WA (US)

(*) Notice: Subject to any disclaimer, the term of this patent is extended or adjusted under 35 U.S.C. 154(b) by 377 days.

(21) Appl. No.: 14/936,828

(22) Filed: Nov. 10, 2015

(65) Prior Publication Data

US 2017/0127997 A1     May 11, 2017

(51) Int. Cl.
*A61B 5/00* (2006.01)

(52) U.S. Cl.
CPC ............ *A61B 5/4362* (2013.01); *A61B 5/486* (2013.01); *A61B 5/6804* (2013.01); *A61B 5/742* (2013.01)

(58) Field of Classification Search
CPC ... A61B 5/1117; A61B 5/1118; A61B 5/1123; A61B 5/4343; A61B 5/6801; A61B 5/11; A61B 5/721; A61B 5/746; A61B 5/7214; A61B 5/4362; A61B 5/486; A61B 5/742; A61B 5/6804
USPC ........................................................ 600/553
See application file for complete search history.

(56) References Cited

U.S. PATENT DOCUMENTS

| | | | |
|---|---|---|---|
| 5,817,035 A | 10/1998 | Sullivan | |
| 6,533,706 B2* | 3/2003 | Morrow | A63B 24/00 482/1 |
| 8,075,500 B2 | 12/2011 | Berger et al. | |
| 8,666,481 B2 | 3/2014 | Harrold et al. | |
| 9,615,777 B2* | 4/2017 | Cloutier | A61B 5/0002 |
| 9,717,457 B2* | 8/2017 | Iuliano | A61B 5/6803 |
| 9,754,470 B2 | 9/2017 | Ten Kate | |
| 9,901,290 B2 | 2/2018 | Najafi et al. | |
| 2008/0319353 A1 | 12/2008 | Howell et al. | |
| 2010/0191154 A1 | 7/2010 | Berger et al. | |
| 2013/0245436 A1 | 9/2013 | Tupin, Jr. et al. | |

* cited by examiner

*Primary Examiner* — Max Hindenburg
(74) *Attorney, Agent, or Firm* — Dorsey & Whitney LLP

(57) ABSTRACT

Embodiments disclosed herein are directed to devices, systems, and methods for monitoring pregnancy of a female pregnant subject. For example, a pregnancy monitoring system can detect movement or motion of a pregnant subject and/or of the fetus in the pregnant subject. Additionally or alternatively, the pregnancy monitoring system can detect internal and/or external source loads applied to the pregnant subject. In an embodiment, the pregnancy monitoring system can compare and/or correlate two or more loads, one to another (e.g., to produce an output that is in part based on such comparison and that is related to the wellbeing of the pregnant subject and/or of the fetus). For example, the pregnancy monitoring system can include a controller that is configured to determine and compare two or more loads based on signals received from one or more sensors that can be positioned on the pregnant subject.

46 Claims, 4 Drawing Sheets

PREGNANCY MONITORING DEVICES, SYSTEMS, AND RELATED METHODS

If an Application Data Sheet (ADS) has been filed on the filing date of this application, it is incorporated by reference herein. Any applications claimed on the ADS for priority under 35 U.S.C. §§ 119, sensors 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

BACKGROUND

Monitoring a state of a pregnant woman and/or of a fetus of the pregnant woman can help prevent or eliminate health risks associated with pregnancy and/or can have health benefits for the newborn and/or for the mother after the delivery. For example, periodic ultrasound check-ups can provide information about health conditions of the fetus and/or of the mother that can be treated and/or ameliorated by interventional therapy that can lead to improved health outcomes for the mother and/or for the newborn after delivery.

Therefore, manufactures, health care providers, and pregnant subjects continue to seek improved devices, systems, and methods for pregnancy monitoring.

SUMMARY

Embodiments disclosed herein are directed to devices, systems, and methods for monitoring pregnancy of a female pregnant subject (e.g., a mammalian female, such as a human female). For example, a pregnancy monitoring system can detect movement or motion of a pregnant subject and/or of a fetus in the pregnant subject. Additionally or alternatively, the pregnancy monitoring system can detect internal and/or external source loads applied to and/or experienced by the pregnant subject. In an embodiment, the pregnancy monitoring system can compare and/or correlate two or more loads, one to another (e.g., to produce an output that is at least partially based on such a comparison and that is related to the wellbeing of the pregnant subject and/or of the fetus). For example, the pregnancy monitoring system can include a controller that is configured to determine and compare two or more loads based on signals received from one or more sensors that can be positioned on the pregnant subject.

Embodiments include a system for monitoring a pregnant subject. The system includes one or more sensors configured to generate one or more signals related to at least an external source load applied to the pregnant subject and to motion of the pregnant subject. The system also includes a controller, which includes control electrical circuitry operably coupled to the one or more sensors and configured to receive the one or more signals therefrom. The control electrical circuitry is configured to distinguish motion of the pregnant subject from the external source load based at least partially on the one or more signals received from the one or more sensors and to generate an output related to one or more of the external source load or the motion of the pregnant subject.

Embodiments also include a wearable system for monitoring a pregnant subject. The wearable system includes one or more wearable elements sized and configured to be worn by the pregnant subject. The wearable system also includes one or more sensors configured to generate one or more signals related to at least an external source load applied to the pregnant subject and to motion of the pregnant subject. At least one of the one or more sensors is carried by the one or more wearable elements. The wearable system includes a controller, which includes control electrical circuitry operably coupled to the one or more sensors and configured to receive the one or more signals therefrom. The control electrical circuitry is configured to distinguish motion of the pregnant subject from the external source load based at least partially on the one or more signals received from the one or more sensors and to generate an output related to one or more of the external source load or the motion of the pregnant subject.

One or more embodiments include a method of monitoring a pregnant subject. The method includes, at a controller, receiving one or more signals from one or more sensors related to at least an external source load applied to the pregnant subject and to motion of the pregnant subject. The method also includes, at the controller, distinguishing motion of the pregnant subject from the external source load applied to the pregnant subject based at least partially on the signals received from the one or more sensors. The method further includes, at the controller, determining at least the external source load applied to the subject at least partially based on the one or more signals from one or more sensors. The method additionally includes generating an output related to at least one of the external source load or the internal source load.

At least one embodiment includes a system for monitoring a pregnant subject. The system includes one or more sensors configured to generate one or more signals related to at least an external source load applied to the pregnant subject. The system further includes a controller, which includes control electrical circuitry operably coupled to the one or more sensors and configured to receive the one or more signals therefrom. The control electrical circuitry is configured to determine a direction of the external source load at least partially based on the one or more signals received from the one or more sensors and to generate an output related to the direction of the external source load.

At least one embodiment includes a wearable system for monitoring a pregnant subject. The system includes one or more wearable elements sized and configured to be worn by the pregnant subject, and one or more sensors configured to generate one or more signals related to at least an external source load applied to the pregnant subject. At least one of the one or more sensors is carried by the one or more wearable elements. The wearable system also includes a controller, which includes control electrical circuitry operably coupled to the one or more sensors and configured to receive the one or more signals therefrom. The control electrical circuitry is configured to determine a direction of the external source load at least partially based on the one or more signals received from the one or more sensors and to generate an output related to the direction of the external source load.

Embodiments also include a method of monitoring a pregnant subject. The method includes, at a controller, receiving one or more signals from one or more sensors related to at least one of an external source load or an internal source load applied to the pregnant subject. The method includes, at the controller, determining a direction of the external source load at least partially based on the one or more signals received from the one or more sensors. Additionally, the method includes generating an output related to at least one of the direction of the external source load or the direction of the internal source load.

At least one embodiment includes a system for monitoring a pregnant subject. The system includes one or more sensors configured to generate one or more signals related to at least one of an internal source load or an external source load applied to the pregnant subject. The system further includes a controller including control electrical circuitry operably coupled to the one or more sensors and configured to receive the one or more signals therefrom. The control electrical circuitry is configured to compare one of the internal source load or the external source load to the other of the internal source load or the external source load and to generate an output related to at least one of the internal source load or the external source load at least partially based on the one or more signals received from the one or more sensors.

Embodiments also include a wearable system for monitoring a pregnant subject. The wearable system includes one or more wearable elements sized and configured to be worn by the pregnant subject. The wearable system also includes one or more sensors configured to generate one or more signals related to at least one of an internal source load or an external source load applied to the pregnant subject. At least one of the one or more sensors is carried by the one or more wearable elements. The wearable system also includes a controller including control electrical circuitry operably coupled to the one or more sensors and configured to receive the one or more signals therefrom. The control electrical circuitry is configured to compare one of the internal source load or the external source load to the other of the internal source load or the external source load and to generate an output related to at least one of the internal source load or the external source load at least partially based on the one or more signals received from the one or more sensors.

At least one embodiment includes a method of monitoring a pregnant subject. The method includes, at a controller, receiving one or more signals from one or more sensors that detect one or more forces associated with at least one of an internal source load or an external source load applied to the pregnant subject. Moreover, the method includes, at the controller, determining at least one of the internal source load or the external source load based at least partially on the one or more signals received from the one or more sensors. The method further includes, at the controller, comparing the internal source load with the external source load. Additionally, the method includes generating an output related to at least one of the external source load or the internal source load.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
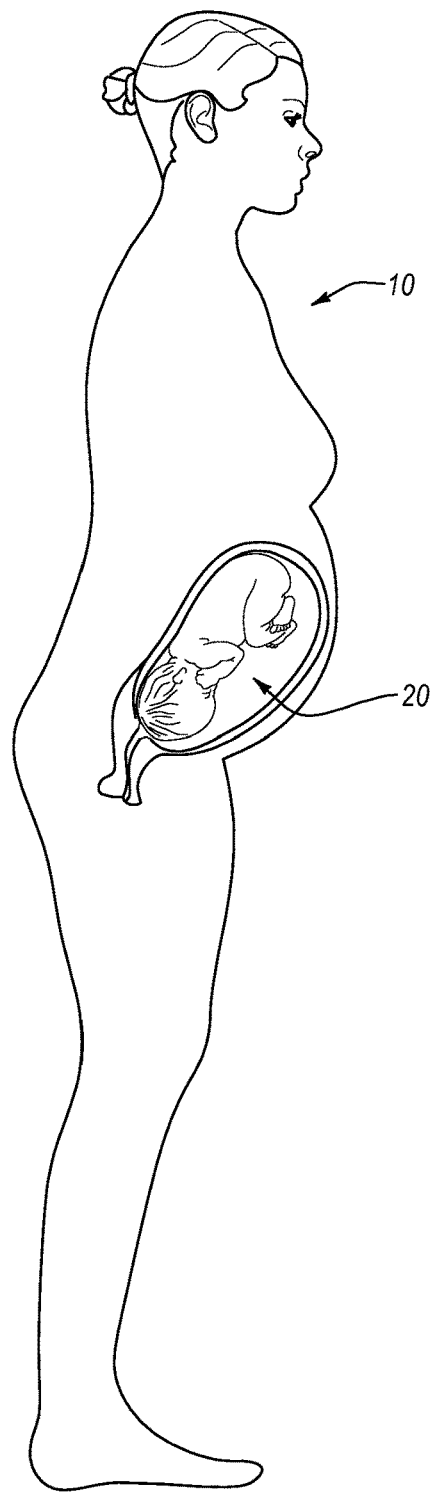
FIG. 1 is a schematic illustration of a pregnant subject.

Embodiments disclosed herein are directed to devices, systems, and methods for monitoring pregnancy of a female pregnant subject (e.g., a mammalian female, such as a human female). For example, a pregnancy monitoring system can detect movement or motion of a pregnant subject and/or of the fetus in the pregnant subject. Additionally or alternatively, the pregnancy monitoring system can detect internal and/or external source loads applied to and/or experienced by the pregnant subject. In an embodiment, the pregnancy monitoring system can compare and/or correlate two or more loads, one to another (e.g., to produce an output that is at least partially based on such a comparison and that is related to the wellbeing of the pregnant subject and/or of the fetus). For example, the pregnancy monitoring system can include a controller that is configured to determine and compare two or more loads based on signals received from one or more sensors that can be positioned on the pregnant subject.

In an embodiment, the controller (e.g., control electrical circuitry of the controller) of the pregnancy monitoring system can compare at least one internal source load to at least one external source load (e.g., compare a load imparted onto the pregnant subject by the fetus to a load imparted onto the exterior of the pregnant subject). For example, the controller can relate the external source load, such as a force or impact applied to the pregnant subject to one or more portions of the fetus inside the pregnant subject impacted by the force. For example, the control electrical circuitry of the controller can correlate one or more of internal or external source load(s) to a position and/or orientation of the fetus in the pregnant subject, which can be at least partially determined based on internal source loads determined by the control electrical circuitry of the controller.

In an embodiment, the control electrical circuitry of the controller of the pregnancy monitoring system can determine vector values (e.g., direction and/or magnitude) of the internal and/or external source loads at least partially based on the signals received from one or more sensors. For example, the control electrical circuitry of the controller can determine a direction of the internal and/or external source loads at least partially by comparing signals received from the sensor(s) and/or information related to the signal(s) (e.g., timing of the received signal(s)). In an embodiment, the controller can compare a time difference between receiving a first signal (or signals) from a first sensor (or a group of sensors) and a second signal (or signals) from a second sensor (or a second group of sensors). Additionally or alternatively, the control electrical circuitry of the controller can compare the time difference between detecting a change in the first signal from the first sensor and detecting a change in the second signal from second sensor. In any event, in an embodiment, the control electrical circuitry of the controller can determine the direction of the load at least partially based on the propagation and detection of the load across multiple sensors.

In an embodiment, the control electrical circuitry of the controller can determine movement of the pregnant subject and/or of the fetus in the pregnant subject. For example, the control electrical circuitry of the controller can determine an amount (e.g., rate) and/or an intensity (e.g., force(s) applied to the pregnant subject) of movement of the fetus at least partially based on the signals received from the sensor(s), which can be related to the internal source loads detected by the sensor(s). For example, the control electrical circuitry of the controller can determine one or more of speed of movement, type of movement (e.g., the fetus turning, kicking, etc., the pregnant subject walking, running, swaying, swimming, etc.), the duration of movement, or combinations of the foregoing. The control electrical circuitry of the controller also can determine a type (e.g., walking, running, driving, etc.) and/or an amount of movement (e.g., speed, quantity of movement per unit time, such as miles per day) for the pregnant subject. Furthermore, the control electrical circuitry of the controller can compare and/or correlate the movement or motion of the pregnant subject to the movement or motion of the fetus inside the pregnant subject.

In an embodiment, the controller can determine or identify an external source load that exceeds a threshold value. For example, the controller can determine that the pregnant subject experienced an impact or an external source load imparted onto the pregnant subject exceeded a threshold value (e.g., threshold magnitude, location of impact, direction of impact, or combinations thereof). In an embodiment, the controller can generate an output related to the external source load that exceeded the threshold value. Furthermore, the generated output can be displayed to a user (e.g., to the pregnant subject) on a suitable display, as described below in more detail.

In an embodiment, the controller can output one or more recommendations related to the determined amount and/or type of movement for the pregnant subject and/or of the fetus. Moreover, in an embodiment, the control electrical circuitry of the controller can compare the amount of movement at a first time (or first time period) to the amount of movement at the second time (or second time period). For example, the control electrical circuitry of the controller can compare the amount of movement of the fetus inside the pregnant subject before detection or determination of the external source load that exceeded a threshold value to the amount of movement of the fetus thereafter (e.g., average amount of movement calculated over a selected period of time).

In an embodiment, the pregnancy monitoring system can include one or more sensors that can be worn by and/or attached to the pregnant subject. For example, one or more sensors can be attached or adhered to the skin of the pregnant subject (e.g., directly to the skin of the pregnant subject), such as to detect internal and/or external source loads applied to the subject. Additionally or alternatively, one or more sensors can be attached to or integrated into a garment that can be worn by the pregnant subject in a manner that the one or more sensors can detect the internal and/or external source loads applied to the pregnant subject.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

FIG. 1 is a schematic illustration of a pregnant subject 10. In particular, a fetus 20 is shown inside the pregnant subject 10. It should be appreciated that the fetus 20 can have any number of orientations in a uterus of the pregnant subject 10, for example, depending on the stage of the pregnancy of the pregnant subject 10. Moreover, the fetus 20 can exhibit various movements or motion of the fetus can vary in the pregnant subject 10, while the fetus remains generally in the same orientation inside the uterus of the pregnant subject 10. As described below in more detail, a pregnancy monitoring system according to one or more embodiments disclosed herein can monitor the motion of the pregnant subject 10 and/or of the fetus 20, such as by monitoring the internal and/or external source loads applied to the pregnant subject 10 and/or by the fetus (e.g., loads that can be imparted onto the pregnant subject 10 by the fetus 20 and/or loads applied to the pregnant subject 10 and by the fetus 20, which originate from or are imparted by external environment). It should be appreciated that, while the pregnant subject 10 is illustrated with a single fetus 20, the pregnant subjects described herein can have any number of fetuses therein.

Figure 2:
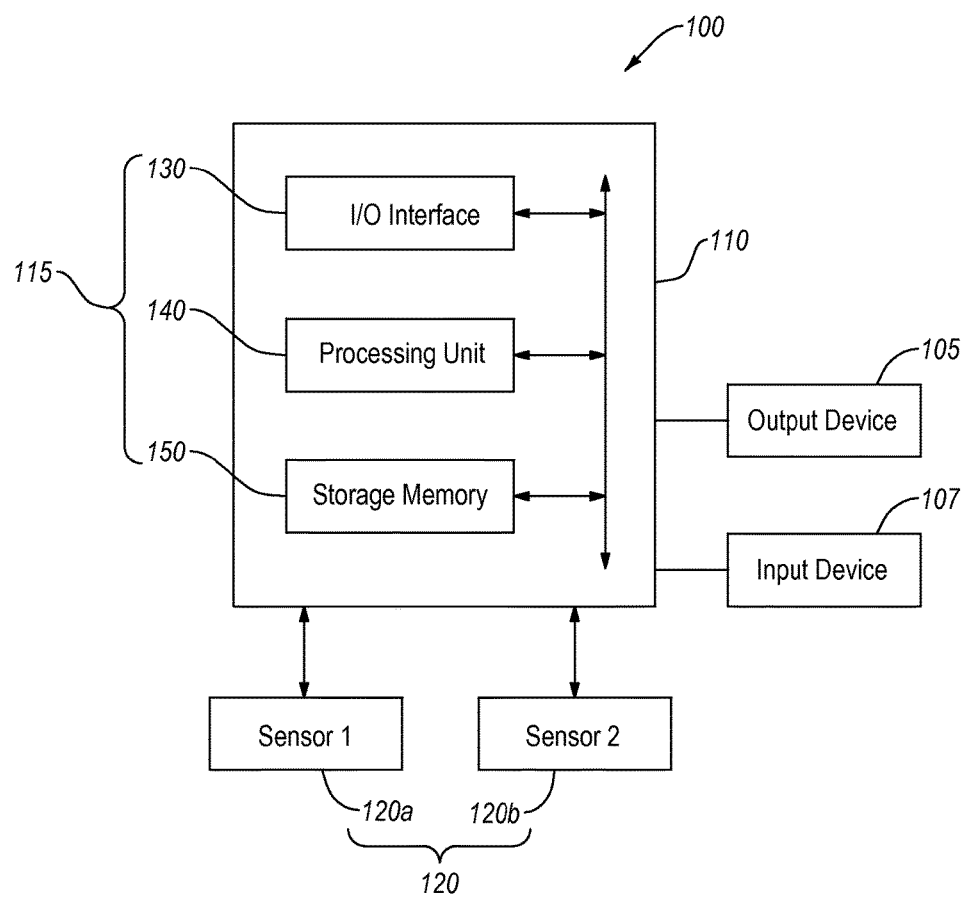
FIG. 2 is a schematic illustration of a pregnancy monitoring system according to an embodiment.

FIG. 2 is a schematic illustration of a pregnancy monitoring system 100 according to an embodiment. The pregnancy monitoring system 100 includes a controller 110 and one or more sensors 120 (e.g., sensors 120a, 120b) operably coupled to the controller 110. The sensors 120 can be arranged in a sensor arrangement and/or a sensor array, as discussed below in more detail. Moreover, the sensors 120 can be positioned on the pregnant subject to detect internal and/or external source loads. In an embodiment, the sensors 120 can include any number of sensors and/or any number of different types of sensors, such as accelerometers, strain sensors, gyroscopes, etc., as described below in more detail. For example, the sensors 120 can be configured to generate one or more signals that can be related to an external source load and/or an internal source load experience by pregnant subject.

The controller 110 can receive and/or send signals to the sensors 120. For example, the controller 110 can receive signals from the sensors 120, which can correspond to the internal and/or external source loads detected by the sensors 120. The controller 110 can receive signals from the sensors 120 that can be related to the movement, position, orientation, or combinations thereof of the pregnant subject or the fetus therein. The controller 110 can process the signals received from the sensors 120 and can generate output related thereto. In an embodiment, the controller 110 can be operably coupled to and/or can include one or more output devices, such as an output device 105, such that at least some of the output generated at the controller 110 can be output or displayed on the output device. For example, the output device 105 can be a visual display (e.g., an LCD display, an OLED display, CRT display, LED display, such as having one or more discrete lighting elements, etc.). Additionally or alternatively, the output device 105 can be and/or can include a sound emitting device, such as a speaker, a tactile device, such as a device configured to vibrate (e.g., a device including a mass that can be moved in a manner that vibrates the device, such as by a changing magnetic field, a motor, etc.). Additionally or alternatively, the output device 105 can be and/or can include a wireless transmitter, configured to transmit the output to an external receiver (e.g., a cell phone, a cellular base station, a computer, a wifi hub, etc.).

Generally the controller 110 can include control electrical circuitry that can be configured and/or programmed to perform one or more acts described herein. In the illustrated embodiment, the controller 110 includes control electrical circuitry 115 that includes an I/O interface 130, a processing unit 140, a storage memory 150, which can be operably coupled together. For example, the controller 110 can receive signals from the sensors 120 at the I/O interface 130 of the control electrical circuitry 115. In some embodiments, the control electrical circuitry 115 of the controller 110 can include or can be operably coupled to one or more A/D converters, which can convert analog signals received from the sensors 120 to digital signals that can be passed from the I/O interface 130 to the processing unit 140 for processing. It should be appreciated that, in some embodiments, the sensors 120 can generate digital signals that can be received at the I/O interface 130 of the control electrical circuitry 115 of the controller 110.

In an embodiment, the storage memory 150 can store data that is related to the signal(s) received from the sensors 120. For example, the storage memory 150 can store one or more values or magnitudes associated with the signals received from the sensors 120 (e.g., values of or related to internal and/or external source loads sensed or detected by the sensors 120 and/or determined by the control electrical circuitry 115 of the controller 110). Additionally or alternatively, the storage memory 150 can store date and/or time associated with the stored values and/or signals received from the sensors 120. Moreover, the storage memory 150 can include one or more databases, indices, lookup tables, combinations thereof, and the like that can be accessed by the processing unit 140 to process signals received from the sensors 120, as described herein (e.g., the processing unit 140 can compare one or more values of internal and/or external source loads determined form the signals received from the sensors 120 to one or more threshold values stored in the storage memory 150). In an embodiment, the storage memory 150 can include a removable storage medium (e.g., a flash card, a DVD, etc.).

As described below in more detail, the controller 110 can send signals or instructions to one, some, or each of the sensors 120. For example, at least one of the sensors 120 (e.g., pinging sensors 120) can generate a control or identification signal or ping that can be detected by one or more other sensors 120, which can send corresponding signals to the controller 110. For example, the other sensors 120 (e.g., non-pinging sensors 120) can generate signals based on the detected ping or identification signal(s) sensed from the pinging or signaling sensors 120. At least partially based on the signals received from the non-pinging sensors 120, the control electrical circuitry 115 of the controller 110 can determine the position(s) of the pinging sensor(s) 120 relative to one or more other sensors 120 that have generated the signal responsive to the ping of the pinging sensors 120.

In some embodiments, the processing unit 140 can include a processor including processing electrical circuitry. Additionally or alternatively, the processing unit 140 can include a memory (e.g., random access memory (RAM), cache memory, etc.) operably coupled to the processor. For example, the processor can receive and execute or process instructions and/or process data and generate an output, as described herein. In an embodiment, the instructions can be stored in the random access memory and/or in the storage memory 150. In an embodiment, the processing unit 140 can include one or more field programmable gate arrays (FPGAs), which can be configured to process data received from the I/O interface 130, according to the processes and steps or act described herein.

In an embodiment, the control electrical circuitry 115 of the controller 110 can distinguish the internal source loads from external source loads based at least partially on signals from the sensors 120. The controller 110 can determine the direction of the load, such as load directed from inside the pregnant subject toward an outer environment, load directed from environment external to the pregnant subject toward the pregnant subject, direction of the load relative to the pregnant subject, such as relative to the torso the pregnant subject. The direction can include one or more of a normal component substantially perpendicular to a surface of the pregnant subject (inwardly or outwardly directed), or a lateral component substantially parallel to a surface of the pregnant subject. For example, the control electrical circuitry 115 of the controller 110 can compare signals from two of the sensors 120 to determine the direction of the load. Moreover, in a similar manner, the control electrical circuitry 115 of the controller 110 can determine the location of the load or impact on the pregnant subject.

In an embodiment, two or more of the sensors 120 can be directionally positioned relative to each other and/or relative to the skin of the pregnant subject (e.g., such that a first of the sensors 120 is positioned closer to the skin, while a second of the sensors 120 is positioned farther from the skin of the pregnant subject). For example, the first sensor of the sensors 120 can be positioned relative to the second sensor of the sensors 120 such that the external source load can be detected by the second sensor before the first sensor and/or such that the internal source load can be detected by the first sensor before the second sensor. Hence, the controller 110 can determine or distinguish the external source load from the internal source load based on a time difference in receiving signals from the first and second sensors of the sensors 120.

In an embodiment, the sensors 120 can substantially continuously generate and/or transmit the generated signals that can be received at the controller 110. In an embodiment, the control electrical circuitry 115 of the controller 110 can distinguish the external source load from internal source load by comparing the time difference between the signals received from the first sensor and second sensor of the sensors 120, where the signals are substantially the same.

For example, the signals received from the first sensor and from the second sensor can be represented by a signal amplitude relative a time (e.g., as a sine wave or irregular wave). The control electrical circuitry 115 of the controller 110 can determine a time shift required to generally match or generally align the signals received from the first sensor to the signals received from the second sensor, such that the amplitudes and/or the signal shapes align with each other. For example, shifting a first signal from the first sensor forward relative to time to align with a second signal from the second sensor can be correlated by the control electrical circuitry 115 of the controller 110 to an external source load. By contrast, shifting the first signal (from the first sensor) backward relative to time to align with the second signal from the second sensor can be correlated by the control electrical circuitry 115 of the controller 110 to an internal source load.

In some embodiments, the controller 110 can include a filter (e.g., digital and/or analog filter that can filter out at least some frequencies of the signal(s) received from the sensors 120. For example, the sensors 120 can generate signals responsive to internal and/or external loads that may not be of interest to monitoring by the pregnancy monitoring system 100 (e.g., noise signals produced during operation of the sensors 120). The filter(s) can filter the noise, such that the processing unit 140 can process a filtered signal (e.g., to determine or distinguish the internal and external source loads). Additionally or alternatively, the control electrical circuitry 115 of the controller 110 can compare a change in signal received from two or more of the sensors 120. For example, the change in first signal ($\Delta S_1$) from the first sensor, which exceeds a threshold value, can be compared to a change in second signal ($\Delta S_2$) from the second sensor, which exceeds the threshold value. In particular, for example, the control electrical circuitry 115 of the controller 110 can compare a time of receiving the first signal that represented or formed the basis of the $\Delta S_1$ with a time of receiving the second signal that represented or formed the basis of the $\Delta S_2$ to determine or distinguish the internal source force from the external source force.

Additionally or alternatively, the sensors 120 can be positioned at different locations on the body of the pregnant subject. For example, as described below in more detail, the sensors 120 can be positioned about the torso of the pregnant subject, about the abdomen of the pregnant subject, about the waistline of the pregnant subject, or combinations of the foregoing. The control electrical circuitry 115 of the controller 110 can compare the time a signal was received from the sensors 120 at different locations or positions on the torso of the pregnant subject to determine direction of the load and/or to distinguish the internal from external source loads that correspond to the received signals.

For example, the control electrical circuitry 115 of the controller 110 can compare the time a first signal is received from a sensor that is located on or near the back of the pregnant subject to the time a second signal received from a sensor located on or near the front of the pregnant subject (e.g., on the abdomen of the pregnant subject) to determine the direction of the load. The control electrical circuitry 115 of the controller 110 can distinguish the load(s) directed generally from the back toward the front from the load(s) directed generally from the front toward the back. The control electrical circuitry 115 of the controller 110 additionally or alternatively can compare the time of receiving a third signal from a sensor on the left side of the pregnant subject to the time of receiving a fourth signal from a sensor on an opposite side (e.g., on the right side) of the pregnant subject to determine or distinguish the direction of the load directed from the left side toward the right side of the pregnant subject or vice versa.

Similarly, the control electrical circuitry 115 of the controller 110 can distinguish or determine the direction of the load by comparing a strength of the signal. For example, the control electrical circuitry 115 of the controller 110 can compare the strength of a first signal received from a sensor on the back of the pregnant subject to the strength of a second signal received from a sensor on the front of the pregnant subject to determine the direction of the load. The control electrical circuitry 115 of the controller 110 can determine that the load is directed from the back side of the pregnant subject to the front side of the pregnant subject when the first signal is stronger or vice versa. The control electrical circuitry 115 of the controller 110 additionally or alternatively can compare the strength of a third signal from a sensor on the left side of the pregnant subject to the strength of a fourth signal from a sensor on the right side of the pregnant subject to determine or distinguish the direction of the load from left side toward the right side of the pregnant subject or vice versa. For example, the control electrical circuitry 115 of the controller 110 can determine that the third signal is stronger than the fourth signal and can correlate the third and fourth signals to a load direction that is generally from the left side toward the right side of the pregnant subject.

As described above, in some embodiments two or more of the sensors 120 can be stacked in a manner that the control electrical circuitry 115 of the controller 110 can determine the direction of the load and/or can distinguish an internal source load (e.g., movements and/or kicking of the fetus) from an external source load (e.g., impact experienced by the pregnant subject). In an embodiment, the control electrical circuitry 115 of the controller 110 can determine direction of the load and/or distinguish internal from external loads by comparing signals received from multiple sensors positioned at different locations on the pregnant subject. Additionally or alternatively, the control electrical circuitry 115 of the controller 110 can determine direction of the load and/or distinguish internal from external loads by comparing signals received from multiple sensors located at the same location and/or at multiple locations on the pregnant subject but having different spatial positions relative to the outer surface of the skin of the pregnant subject. For example, the control electrical circuitry 115 of the controller 110 can receive signals from one or more stacked sensor assemblies and can distinguish internal from external source load and/or can determine direction of the load(s) based on such signals. Moreover, the control electrical circuitry 150 of the controller 110 can process signals from a stacked sensors assembly in a similar manner as described above, to determine the direction of the load and/or to distinguish internal from external source loads detected by the stack sensor assembly or assemblies.

In any event, in an embodiment, the controller 110 can receive input (e.g., at the I/O interface 130), such as signals from the sensors 120. Additionally or alternatively, the controller 110 can receive input(s) for one or more input devices, such as from an input device 107. The input device 107 can be and/or can include any number of suitable input devices. For example, the input device 107 can include one or more input buttons, such as a keyboard (e.g., a physical keyboard, a virtual keyboard, such as a keyboard displayed on an output device, such as on output device 105, etc.). Additionally or alternatively, the input device 107 can be and/or can include a microphone, a camera, etc. Moreover, in an embodiment, the controller 110 can receive information from one or more other controllers and/or computers (e.g., from a personal electronic device, such as a smart phone, a smart watch, etc.). Hence, for example, the input device 107 can be and/or can include another controller and/or computer.

Figure 3:
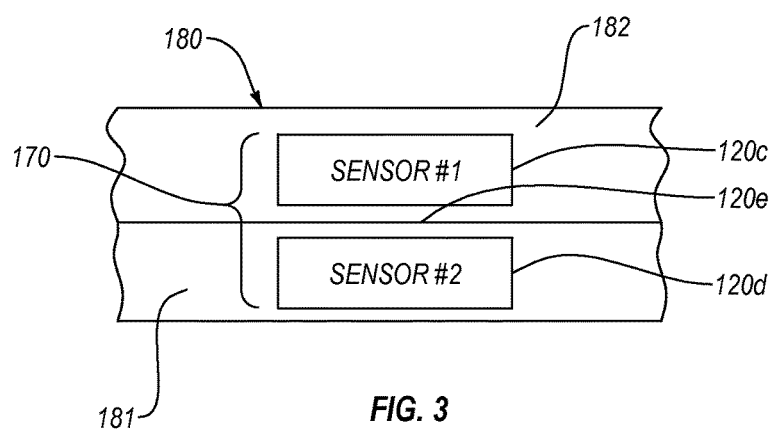
FIG. 3 is a schematic illustration of a stacked sensor assembly attached to a backing according to an embodiment.

FIG. 3 illustrates a stacked sensor assembly 170 according to an embodiment, which can be incorporated in any of the pregnancy monitoring systems disclosed herein. In the illustrated embodiment, the stacked sensor assembly 170 includes sensors 120*c* and 120*d* positioned near each other, such that, the sensor 120*c* can be positioned closer to a reference location on the pregnant subject than the sensor 120*d* or vice versa. For example, the reference location can be an outer surface of the skin of the pregnant subject.

In an embodiment, the stacked sensor assembly 170 can be embedded in and/or attached to a backing 180. In particular, for example, the backing 180 can secure the stacked sensor assembly 170 to the pregnant subject. As described below in more detail, the backing 180 can be attached to or worn by the pregnant subject. For example, the backing 180 can be attached and/or incorporated into a garment that can be worn by the pregnant subject. Additionally or alternatively, the backing 180 can include an adhesive backing (e.g., pressure sensitive adhesive) and can be temporarily attached or temporarily adhered directly to the skin of and/or garment worn by the pregnant subject.

Generally, the backing 180 can include any number of layers and/or materials or material combinations, which can vary from one embodiment to the next. In an embodiment, the backing 180 can include two sheets or layers 181, 182 connected and/or bonded together, each of which can respectively secure the sensors 120*c* and 120*d*. Alternatively, the sensors 120*c*, 120*d* can be positioned and/or embedded in a generally monolithic material (e.g., in a thermoplastic material). Moreover, in an embodiment, the material securing the sensors 120*c*, 120*d* (e.g., the backing 180) can be generally flexible. For example, when attached to skin of the pregnant patient, the material securing the sensors 120*c*, 120*d* to the skin can flex, stretch, bend, or combinations thereof as the skin of the pregnant subject flexes and/or bends, stretches, bends, etc.

In any event, the backing 180 can secure the stacked sensor assembly 170 to the patient, such as by attaching to the skin of the patient, to the clothing of the patient, combinations thereof, etc. Hence, in an embodiment, the stacked sensor assembly 170 can detect or sense internal and/or external forces applied to the pregnant subject, which can be transmitted from the attaching medium (e.g., from the skin of the pregnant subject, from the garment worn by the pregnant subject, etc.). In any event, the stacked sensor assembly 170 can detect or sense the internal and/or external source load(s) in a manner that facilitates distinguishing internal from external source loads at the controller receiving signals from the sensors of the stacked sensor assembly 170 (e.g., from the sensors 120*c* and 120*d*), as described below in more detail. Moreover, in an embodiment, the stacked sensor assembly 170 or arrays or arrangements of sensor assemblies can arranged and/or configured in a manner that facilitates determining the direction of the internal and/or external source force(s) at the controller receiving signals therefrom.

Generally, as described above, one or more sensors operably coupled to the controller (e.g., to the control electrical circuitry of the controller) can generate one or more signals that can be related to the external source load applied to the pregnant subject. More specifically, in an embodiment, the control electrical circuitry of the controller can determine and/or distinguish the external source load from one or more other loads at least partially based on the signals received from the sensor(s) of the stacked sensor assembly 170 (e.g., in a similar manner as described above in connection with sensors positioned at different relative locations on the pregnant subject). For example, the control electrical circuitry of the controller can be configured to distinguish the external source load(s) from the internal source load(s), such as to distinguish the external source loads from loads generated by the pregnant subject (e.g., during movement of the pregnant subject).

For example, sensors that are operably coupled to the controller can include a first sensor positionable at a first distance relative to an outer surface of the skin of the pregnant subject, and a second sensor can be positionable at a second distance relative to the outer surface of the skin of the pregnant subject, which is greater than the first distance. As such, in an embodiment, the control electrical circuitry of the controller can be configured to distinguish the internal source load from the external source load at least partially based on one or more of a difference in time between the respective sensing signals received from the first sensor and from the second sensor. Additionally or alternatively, the control electrical circuitry of the controller can distinguish between the internal and external source loads based on the difference in strength of the signals received from the first and second sensors.

In an embodiment, at least one of the sensors of the stacked sensor assembly 170 can detect or sense force before at least one other sensor of the stacked sensor assembly 170. For example, the sensor 120*d* can be positioned closer to the skin of the pregnant subject than sensor 120*c* (e.g., the layer 181 can be attachable to the skin and/or to the clothes of the pregnant subject). Responsive to external source force, for example, the signal from the sensor 120*c* can be received or detected by the controller before the signal from the sensor 120*d*.

In an embodiment, the sensors of the stacked sensor assembly 170, such as the sensors 120*c*, 120*d*, can be positioned and/or spaced relative to each other in a manner that attenuates and/or dampens the force transmitted from one sensor to another. In other words, for example, the force vectored in a direction from a first sensor toward a second sensor (e.g., from the sensor 120*c* to the sensor 120*d* or vice versa) can be experienced or sensed by the first sensor to a greater degree than by the second sensor. For example, the stacked sensor assembly 170 can include material that can reduce the degree by which the second sensor experiences or senses the force. For example, such material can be positioned between the first and second sensors (e.g., between the sensors 120*c* and 120*d*). In an embodiment, a vibration dampening and/or signal attenuating material 120*e* can be positioned between the sensors 120*c* and 120*d* (e.g., material that can reduce an amplitude of a source load vibration and/or reduce a temporal frequency of a source load vibration). Alternatively or additionally, the backing 180 can include or comprise the vibration dampening material and/or attenuating material (e.g., foam, gel, etc.). In any event, according to an embodiment, the material 120*e* positioned between the sensors 120*c* and 120*d* can be configured to reduce amplitude of vibration(s) or oscillation(s) associated with a source load (e.g., a wave produced by the source load and traveling in and/or through the stacked sensor assembly 170).

It should be appreciated that the stacked sensor assembly 170 can include any number of sensors (e.g., stacked and/or positioned generally one over another, such as to place the sensors at different locations outward from the skin of the pregnant subject when the stacked sensor assembly 170 is secured or attached to the pregnant subject). Moreover, the stacked sensor assembly 170 can include any number of different types of sensors, which can have any number of suitable relative arrangements as well as any number of arrangements relative to the pregnant subject. For example, the stacked sensor assembly 170 can include any number of accelerometers, strain sensors, micro-impulse sensors, ultrasound sensors (e.g., ultrasound transceiver(s)), heartbeat sensor(s), or combinations of the foregoing.

Figure 4A:
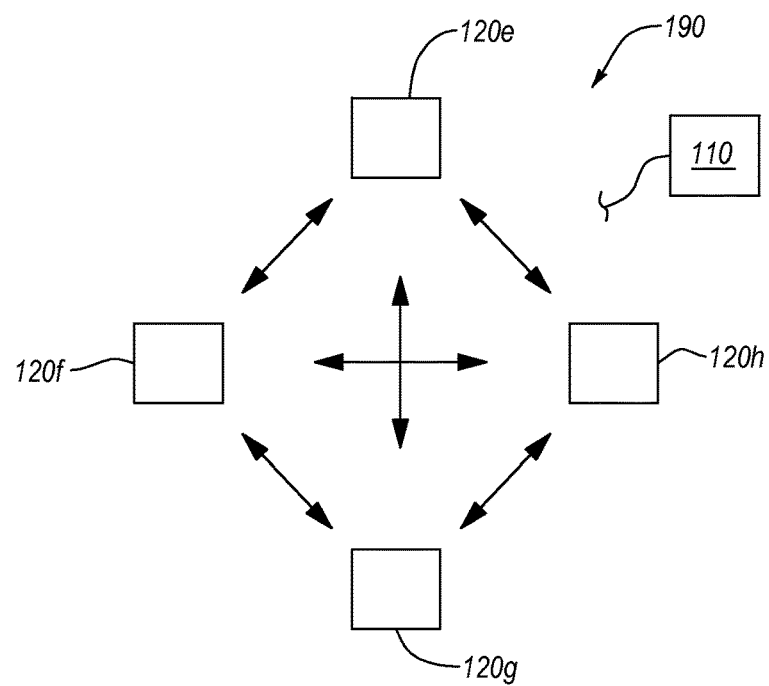
FIG. 4A is a schematic illustration of a sensor arrangement for a pregnancy monitoring system according to an embodiment.

In some embodiments, an array or arrangement of sensors can be configured to determine direction of the internal and/or external source loads (e.g., as described above). Moreover, the sensors in the arrangement can be configured to detect and/or facilitate detection or determining relative positions of the sensors. FIG. 4A is a schematic diagram of an embodiment of a sensor arrangement 190 that includes sensors 120e-120h. The sensors 120e-120h can include any sensor described herein. It should be appreciated that the sensor arrangement 190 can be an array of sensors (e.g., sensors arranged in a selected and/or organized or ordered manner) and/or the sensors comprising the sensor arrangement can be randomly arranged relative to one another.

Generally, one, some, or each of the sensors 120e-120h can be operably coupled to the controller 110, and the controller 110 can receive one or more signals therefrom. As mentioned above, in an embodiment, one, some, or each of the sensors 120e-120h can emit an identification signal or ping that can be detected by one or more of the other sensors in the sensor arrangement 190. For example, any of the sensors 120e-120h can be configured to periodically emit a distinct identification signal or ping (e.g., an electromagnetic or ultrasound pulse of a selected or determined frequency, a pulse generating a detectable vibration, such as vibration transferable along the skin of the pregnant patient, etc.). In any event, in an embodiment, one, some, or each of the sensors 120e-120h can emit or generate identification signal(s) that can be detected by one or more other sensors in the sensor arrangement 190. In an embodiment, the ping or identification signal can be a sound wave (e.g., a sound wave outside of the range that a typical human can hear, such as a sound wave below 20 Hz).

Additionally or alternatively, in an embodiment, the control electrical circuitry of the controller 110 can operate or direct operation of any of the sensors 120e-120h to generate identification signal(s) at one or more selected times. Furthermore, in an embodiment, the control electrical circuitry of the controller 110 can determine and/or distinguish a signal (e.g., an electrical signal) received from the sensors 120e-120h that was generated responsive to the sensing or detecting one or more identification signals from any of the sensors 120e-120h.

In an embodiment, the control electrical circuitry of the controller 110 can determine relative positions and/or arrangement of the sensors 120e-120h. For example, the control electrical circuitry of the controller 110 can determine the distance between the sensors emitting the identification signal and the sensor(s) detecting the identification signal by determining the time difference between the emission of the identification signal and detection thereof. In an embodiment, the control electrical circuitry of the controller 110 can determine the distance at least partially based on the time difference between emission and detection of the identification signal and based on a known (e.g., stored in a memory and/or determined by the control electrical circuitry of the controller 110) and/or constant factor related to a speed of travel of the identification signal in one or more media (e.g., air, skin, etc.) as detected by the detecting sensor.

Hence, in an embodiment, the control electrical circuitry of the controller 110 can determine the distances from a signaling sensor to other sensors of the sensor arrangement 190. Moreover, the electrical circuitry of the controller 110 can iteratively and/or repeatedly determine distances from different signaling sensors and other sensors. For example, the control electrical circuitry of the controller 110 can direct the sensor 120e to emit an identification signal that can be detected by the sensors 120f-120h, and at least partially based on the signals received from the sensors 120f-120h, the control electrical circuitry of the controller 110 can determine the distance from the sensor 120e to each of the respective ones of the sensors 120f-120h. Similarly, the control electrical circuitry of the controller 110 can direct the sensors 120f to emit an identification signal and at least partially based on the signal received from the sensors 120e, 120g, 120h the control electrical circuitry of the controller 110 can determine the distance from the sensor 120f to each of the sensors 120e, 120g, 120h. By selecting different signaling sensors from the sensor arrangement 190 (e.g., such that only a single sensor emits identification signal at a time), the control electrical circuitry of the controller 110 can determine relative distances between the sensors of the sensor arrangement 190. Moreover, at least partially based on the determined relative distances between the sensors of the sensor arrangement 190, the control electrical circuitry of the controller 110 can determine relative positions thereof.

In an embodiment, the control electrical circuitry of the controller 110 can determine the direction of a load (e.g., of the internal and/or external source load) at least partially by comparing the time of receiving a signal from the various sensors of the sensor arrangement 190. For example, the control circuitry of the controller 110 can include or store information about relative positions of and/or distances between the sensors of the sensor arrangement 190. Hence, in an embodiment, the control electrical circuitry of the controller 110 can determine the direction of the load at least partially by comparing times at which signals from different sensors of the sensor arrangement 190 are received by the control electrical circuitry of the controller 110. Furthermore, as described above, the control electrical circuitry of the controller 110 can determine the direction of the load by comparing the strength of the signals received from the sensors 120e-120h that are positioned at different locations relative to one another and to the pregnant subject.

Figure 4B:
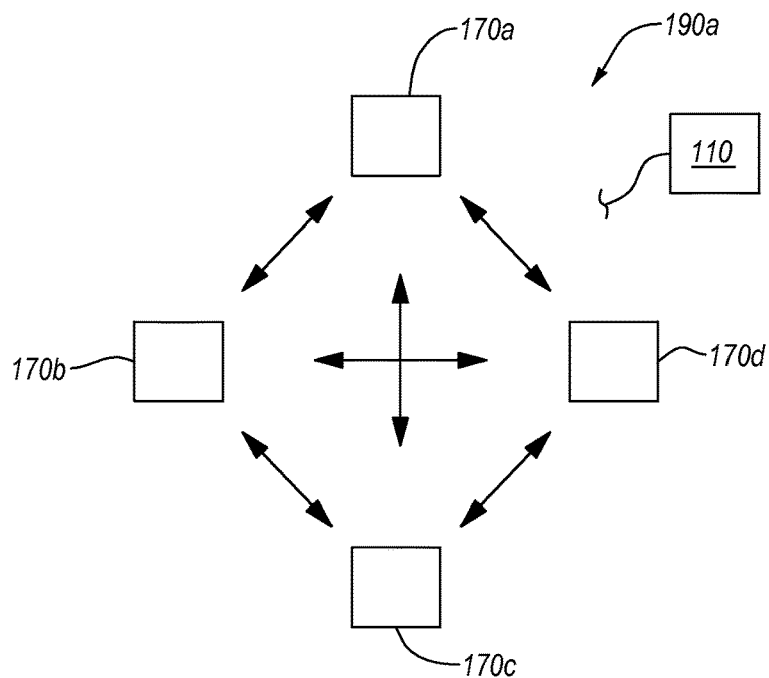
FIG. 4B is a schematic illustration of a sensor arrangement for a pregnancy monitoring system according to another embodiment.

In an embodiment, the sensor array and/or arrangement can include one or more stacked sensor assemblies. FIG. 4B is a schematic diagram of a sensor arrangement 190a that includes multiple stacked sensor assemblies, according to an embodiment. Except as described herein, the sensor arrangement 190a and its elements and component can be similar to or the same as the sensor arrangement 190 (FIG. 4A) and its corresponding elements and components.

In the illustrated embodiment, the sensor arrangement 190a includes stacked sensor assemblies 170a-170d. For example, one, some, or each of the stacked sensor assemblies 170a-170d can include at least one sensor configured to emit or generate a ping or an identification signal. Accordingly, the controller 110 can receive signals from corresponding sensors of the stacked sensor assemblies 170a-170d, which can detect identification signals and can determine relative distances and/or positions of the stacked sensor assemblies 170a-170d, in a similar manner as described above in connection with FIG. 4A (e.g., a signaling sensor that emits an identification sensor can be associated and/or collocated with other sensors of a sensor stack assembly). Accordingly, for example, the control electrical circuitry of the controller 110 can determine or distinguish external source load(s) from internal source load(s) and can determine a direction of the internal and external source load(s).

It should be appreciated that any of the stacked sensor assemblies in the sensor arrangement 190a (e.g., the stacked sensor assemblies 170a-170d) can include and number of different types of sensors, which can vary from one embodiment to the next. Moreover, the sensor arrangement 190a can include any number of stacked sensor assemblies that can be positioned in any number of suitable arrangements. Also, as described above, the sensors and/or sensor assemblies can be positioned about the pregnant subject (e.g., about the torso of the pregnant subject, the abdomen of the pregnant subject, about one or more limbs of the pregnant subject, etc.) and can be attached directly to the skin of the pregnant subject and/or attached to and/or embedded in a garment worn by the pregnant subject.

Figure 5:
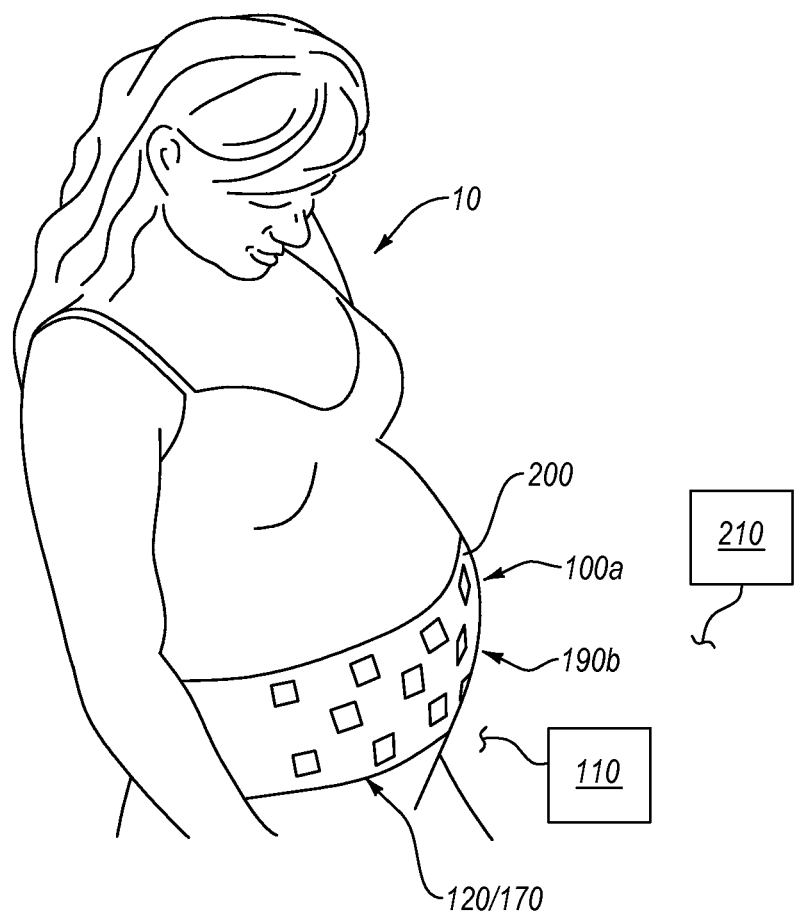
FIG. 5 is a schematic illustration of a pregnancy monitoring system according to an embodiment.

FIG. 5 is a schematic illustration of a pregnancy monitoring system 100a on the pregnant subject 10, according to an embodiment. The pregnancy monitoring system 100a can include one or more load sensitive elements (e.g., the sensors 120 and/or sensor stack assemblies 170) that can be attached to the skin of the pregnant subject 10 directly and/or can be incorporated into a wearable garment, such as garment wearable garment 200. In the illustrated embodiment, the pregnancy monitoring system 100a includes a sensor arrangement 190b that can be included in or on (e.g., secured to and/or embedded in) one or more wearable elements, such as wearable garment 200.

Generally, the pregnancy monitoring system 100a can include any number of wearable elements that can be positioned on the pregnant subject 10 at any number of suitable locations. In an embodiment, the wearable garment 200 can be stretchable and/or elastic, such as to be positioned in contact with the skin of the pregnant subject 10. Alternatively or additionally, wearable elements (e.g., the wearable garment 200) can include an adhesive (e.g., pressure sensitive adhesive) that can be configured to removably attach the wearable element(s) (together with the sensors 120) to the pregnant subject 10. For example, the wearable garment 200 can at least partially wrap about the abdomen of the pregnant subject 10.

As mentioned above, the sensor arrangement 190b can include any number of sensors 120 and/or stacked sensor assemblies 170, which can be of any number of different types and can be positioned and/or arranged at any number of suitable locations relative to the pregnant subject 10. Moreover, the sensors 120 and/or stacked sensor assemblies 170 can be operably coupled to the controller 110. In an embodiment, the controller 110 can be attached to or incorporated with the wearable garment 200. Alternatively, the controller 110 can be positioned outside of the wearable garment 200. Generally, the sensor arrangement 190b can include any of the sensors 120 and/or stacked sensor assemblies 170 described herein, which can detect the load and generate corresponding signals (received at the controller 110), in a manner described herein.

In an embodiment, the controller 110 can include or can be operably coupled (e.g., wired or wirelessly) to an output device, such as a display. More specifically, the display can be configured to display output from the processing unit of the control electrical circuitry of the controller 110. Additionally or alternatively, the controller 110 can be operably coupled (e.g., wired or wirelessly, such as over a Bluetooth connection, over a wireless network, such as WiFi network, over the Internet, etc.) to one or more personal electronic devices, such as a personal electronic device 210, which can be and/or can include a smartphone, tablet, personal computer, etc., and can send information and/or notifications to the controller 110. In an embodiment, the personal electronic device can include a display. For example, the personal electronic device 210 can receive and display output from the controller 110.

As described above, the controller 110 can receive signals from the sensor arrangement 190b and can distinguish internal source load from external source load and/or can determine direction of the load at least partially based on the received signals. In an embodiment, the control electrical circuitry of the controller 110 can be configured to compare external source load to internal source load. For example, the control electrical circuitry of the controller 110 can compare the position or location of the external source load on the pregnant subject relative to the position or location of the internal source load thereon. Alternatively or additionally, the control electrical circuitry of the controller 110 can compare the direction and/or magnitude of the external source load to the direction and/or magnitude of the internal source load. In some embodiments the controller 110 can compare characteristics of an internal load measured at one time to those of an external load measured at a different time. For example, the controller 110 can compare a current load measurement to stored measurements acquired at an earlier time. In some embodiments, the controller 110 can determine whether a measured load corresponds to an internal source or an external source by postulating an internal source location or an external source location and comparing characteristics of the loading from the postulated source to the measured loading.

In an embodiment, at least partially based on the detected external source load and the signals generated by the sensors 120 of the sensor arrangement 190b that detected the external source load, the control electrical circuitry of the controller 110 can determine that the pregnant subject 10 experienced an impact (e.g., an impact that is below a threshold value or an impact at or above the threshold value). Moreover, the control electrical circuitry of the controller 110 can correlate the position and/or location of the load or impact on the pregnant subject 10 to a position or orientation of the fetus inside the pregnant subject 10 and/or to one or more parts thereof. For example, the controller 110 can correlate the location of the impact or external source load with the pregnant subject 10 (e.g., relative to the body parts and/or locations thereof of the pregnant subject 10) at least partially based on the determined direction of the external source load, which the controller can determine in a manner described herein. In some embodiments, the threshold value can be dependent on the proximity of the load location to the fetus or to a specified portion thereof. For example, an alert threshold for a load applied near the head of a fetus can be set to a lower value than the alert threshold for loads not near the fetus, or near a leg of the fetus.

For example, the control electrical circuitry of the controller 110 can be configured to determine a force imparted on at least one portion of the fetus. Additionally or alternatively, the control electrical circuitry of the controller 110 can be configured to determine proximity between a position of the external source load applied to the pregnant subject 10 and a position of a portion of the fetus or a portion of the fetus. For example, the control electrical circuitry of the controller can be configured to determine a distance between an impact on the pregnant subject 10 from an external force and a portion of the fetus, such as a limb and/or torso of the fetus.

Moreover, the control electrical circuitry of the controller 110 can determine a force imparted on the fetus and/or one or more portions thereof, at least partially based on one or more signals received from the sensor(s) 120 and/or based on input related to internal source load(s) applied to the pregnant subject 10. For example, the pregnant subject 10 can enter into the controller 110 the position and/or orientation of the fetus, which can be associated with a sensed or detected external source load or impact (e.g., when the external source load exceeds a threshold value). Hence, for example, the control electrical circuitry of the controller 110 can determine the impact applied to the fetus from the external source load at least partially based on the input received from the pregnant subject 10 and/or on the input or signals received from the sensor(s).

In an embodiment, signal(s) from one or more sensors 120 can be related to the position and/or orientation of the fetus inside the pregnant subject 10. Alternatively or additionally, the control electrical circuitry can determine or estimate position and/or orientation of the fetus inside the pregnant subject 10 based on the internal source forces detected or sensed by one or more sensors 120. For example, the control electrical circuitry of the controller 110 can associate sensed or detected internal source load with kicks of the fetus and can determine corresponding position(s) of the fetus. In an embodiment, the control electrical circuitry of the controller 110 can be configured to substantially continuously determine the position of the fetus, motion of the fetus, orientation of the fetus, or combinations thereof (e.g., relative to the pregnant subject 10). Furthermore the control electrical circuitry of the controller 110 can store data in memory that is related to the determined the position of the fetus, motion of the fetus, orientation of the fetus, or combinations thereof.

Generally, the controller 110 can receive inputs from any number of suitable input devices (e.g., the controller 110 can receive input from various sensors in the form of one or more signals). Furthermore, in an embodiment, a user (e.g., the pregnant subject 10) can enter information or input into the controller 110 (e.g., the control electrical circuitry of the controller can receive information or input from the user), such as information that can be related to the position of the fetus in the pregnant subject 10, the orientation of the fetus in the pregnant subject, motion of the fetus in the pregnant subject, or combinations thereof. For example, the control electrical circuitry of the controller 110 can include and/or can be operably coupled to an input device (e.g., a keyboard or a virtual keyboard, such as a keyboard that can be displayed on a touch screen display that can receive input from a user, microphone, etc.). Moreover, in an embodiment, the input can be entered at a personal electronic device of the user, such as at the personal electronic device 210, and can be sent thereby to the controller 110 (which can be operably coupled thereto).

In an embodiment, the control electrical circuitry of the controller 110 also can compare information on the position and/or orientation of the fetus received from a user with the position and/or orientation of the fetus determined by the control electrical circuitry of the controller 110 based on one or more signals received from the sensor(s) sensors 120. For example, the pregnant subject 10 can enter information or input that is related to internal source load applied to the pregnant subject (e.g., the load(s) applied to the pregnant subject 10 due to movement(s) or motion of the fetus). In an embodiment, at least partially based on the entered or input position and/or orientation of the fetus (received from a user), the control electrical circuitry of the controller 110 can calibrate and/or adjust determinations of the position and/or orientation of the fetus that is determined from one or more signals from the sensor(s) sensors 120. For example, the control electrical circuitry of the controller 110 can be configured to calibrate at least some of the sensors 120 (that are operably coupled thereto) at least partially based on the comparison of the information received from the user with the internal source load determined at least partially based on the signal(s) received from the sensor(s) sensors 120.

Similarly, the control electrical circuitry of the controller 110 can receive input or information from a user (e.g., from the pregnant subject 10), which can be related to external source load(s). In an embodiment, the control electrical circuitry of the controller 110 can be configured to compare the received information that is related to the external source load (e.g., location of an impact, direction of the load, etc. received from the pregnant subject) to the external source load that is determined at least partially based on the one or more signals received from the one or more sensors 120. For example, the control electrical circuitry of the controller 110 can calibrate at least some of the one or more sensors 120 at least partially based on the comparison of the received information (e.g., from the pregnant subject 10) to the external source load to the external source load that is determined at least partially based on the signal(s) received from the sensor(s) sensors 120.

In an embodiment, the controller 110 can determine and output a recommendation at least partially based on and/or related to the signal(s) received from the sensors 120 and/or from input received from a user (e.g., from the pregnant subject 10). For example, the controller 110 can include and/or reference a lookup table, an index, a database, combinations thereof, and the like. In an embodiment, the database or a similar structure can include and/or relate input received from the sensors 120 and/or from the user to values and/or recommendations associated with the input. Hence, the controller 110 can output one or more recommendations that can be related to the internal and/or external source loads.

In an embodiment, the controller 110 can be configured to output and/or display one or more recommendations that can be related to health of the pregnant subject 10 and/or to the health of the fetus in the pregnant subject 10. For example, the controller 110 can generate and/or output an alert that can be configured to notify a user (e.g., the pregnant subject 10) about a condition and/or event related to the health of the fetus. In an embodiment, the controller 110 can generate an alert when the internal source load and/or the external source load exceed a threshold value. For example, the an impact applied to the pregnant subject 10 can be detected as an external source load that exceeds a threshold value for impacts, and the controller 110 can generate an alert informing the pregnant subject 10 of the same and/or informing the pregnant subject 10 to seek medical attention. The controller 110 can also detect reduction or diminishment in activity of the fetus inside the pregnant subject 10 as reduction in or diminishment of internal source loads, heartbeat rate, etc., detected by the sensors 120 and can alert the pregnant subject 10 of the same and/or inform the pregnant subject 10 to seek medical attention. Moreover, as described above, the output from the controller 110 can be displayed to the pregnant subject 10 on the display coupled to and/or integrated with the controller 110 and/or on the display of the electronic device (e.g., the controller 110 can push alerts to a selected smart phone, can text alerts, can email alerts, etc.).

In an embodiment, the pregnancy monitoring system 100*a* can generate a visual or tactile alert that can be sensed by the pregnant subject 10 (e.g., the alert can indicate a recommendation for the pregnant subject to seek medical attention). For example, the load-sensitive elements of the pregnancy monitoring system 100*a* can include one or more dye capsules that can be configured to release a visible dye responsive to detecting internal and/or external source loads exceeding a threshold load. Additionally or alternatively, the load-sensitive elements of the pregnancy monitoring system 100*a* can include one or more capsules or elements configured to generate a tactile vibration that can be felt by the pregnant subject 10, responsive to detecting internal and/or external source loads exceeding a threshold load.

As described above, the pregnancy monitoring system can monitor motion of the pregnant subject and/or of the fetus inside the pregnant subject. For example, the pregnancy monitoring system can monitor and/or determine the total amount of motion exhibited by the pregnant subject and/or by the fetus over a selected period of time. Additionally or alternatively, the pregnancy monitoring system can monitor and/or detect the type of motion exhibited by the pregnant subject and/or by the fetus inside the pregnant subject. In an embodiment, the pregnancy monitoring system can store at least some of the data related to the monitored activities of the pregnant subject and/or of the fetus.

Moreover, in an embodiment, the pregnancy monitoring system can alert a user (e.g., the pregnant subject, a medical professional, etc.) after detecting motion that is outside of a selected range and/or above a threshold value. For example, the pregnancy monitoring system can alert the user when the amount of detected motion of the pregnant subject and/or of the fetus (e.g., a total amount over a period of time, an average amount of motion, which can be determined over a period of time and/or can be continuously updated) falls below a threshold value and/or exceeds a threshold value. In an embodiment, the pregnancy monitoring system can alert the pregnant subject to increase or reduce motion via one or more output devices (e.g., displays, speakers etc.). For example, the alert generated by the control electrical circuitry of the controller can notify the pregnant subject to start or stop motion. Moreover, the controller of the pregnancy monitoring system can be operably coupled to a personal electronic device and can send alerts thereto; the personal electronic device can display the received alert information to the pregnant subject.

In an embodiment, the control electrical circuitry of the controller can correlate the motion of the pregnant subject with the motion of the fetus. For example, the control electrical circuitry of the controller can determine a change in the motion of the fetus (e.g., increase or decrease in the motion of the fetus) and can correlate the change of the motion of the fetus with a change in the motion of the pregnant subject (e.g., increase or decrease in the motion of the pregnant subject). Moreover, the control electrical circuitry of the controller can determine a time difference or delay between the change in the motion of the pregnant subject and the change in the motion of the fetus. Hence, for example, the control electrical circuitry of the controller can recommend to or generate an alert for the pregnant subject to increase or decrease motion by a suitable amount that can be targeted to produce a suitable amount of motion of the fetus (e.g., as may be recommended by a health care provider). In some embodiments, such recommendations and/or alerts can be dependent upon a size, position, or orientation of the fetus. For example, motion of the pregnant subject when the fetus is oriented head-up may be more or less preferred than motion when the fetus is oriented head-down.

As described above, the control electrical circuitry of the controller can include a storage that can be configured to store various data. For example, the storage of the control electrical circuitry of the controller can be configured to store data related to the motion of the pregnant subject and/or of the fetus in the pregnant subject. Additionally or alternatively, the storage can be configured to store data that is generated at least partially from the control electrical circuitry of the controller by correlating the motion of the pregnant subject with the motion of the fetus. Moreover, generally, the control electrical circuitry of the controller can be configured to store any data generated herein by the sensors and/or the controller including data that can be generated at least partially from comparison of internal source load to external source load or an impact event with the pregnant subject. For example, the control electrical circuitry of the controller is configured to compare data that is related to one or more of the motion of the fetus or the motion of the pregnant subject, and which is stored before the impact event, to the data that is related to one or more of the motion of the fetus or the motion of the pregnant subject, and which is stored after the impact event. As another example, the controller is configured to generate an alert at least partially based on the comparison of the data that is related to one or more of the motion of the fetus or the motion of the pregnant subject, and which is stored before the impact event, to the data that is related to one or more of the motion of the fetus or the motion of the pregnant subject, and which is stored after the impact event.

As mentioned above, the control electrical circuitry of the controller can be configured to compare data related to the motion of the fetus and/or to the motion of the pregnant subject before and after an impact. For example, the data related to the motion of the fetus and/or to the motion of the pregnant subject. Accordingly, in an embodiment, the controller can compare stored data (e.g., data that was stored before a detected load that exceeded a threshold value), which is related to the motion of the fetus and/or of the pregnant subject, to the motion determined and/or stored after the detection of the load that exceeded the threshold value.

Furthermore, the control electrical circuitry of the controller can be configured to generate and/or output an alert when a determined change in the motion of the pregnant subject and/or of the fetus (or the determined motion of the fetus and/or of the pregnant subject after detection of a selected load) is deferent from the motion before the detected load by a select amount or percentage. For example, if the motion of the fetus after an impact is less than before the impact by a selected amount or percentage, as determined by the control electrical circuitry of the controller, an alert and/or recommendation can be generated and/or output (e.g., displayed) by the control electrical circuitry of the controller, such as to alert the pregnant subject to seek medical attention. Moreover, in an embodiment, the control electrical circuitry of the controller can generate and/or output or display an alert or recommendation when the motion of the fetus is determined to be below or exceeding a threshold value (e.g., when internal source load(s) are determined to be below or exceeding a threshold value).

As described above, the pregnancy monitoring system 100a can include any number of different types of sensors. In an embodiment, the sensors providing load related signals to the controller 110 can be different types of sensors than the sensor providing motion related signals. For example, the controller 110 of the pregnancy monitoring system 100a can receive and/or correlate signals received from accelerometer(s) or other motion sensing sensor with motion; and the controller 110 also can receive and/or correlate signals received from strain gage(s) or other load-sensitive sensor with internal and/or external source load(s) experience by the pregnant subject 10 and/or by the fetus.

It should be appreciated that pregnancy monitoring system 100a can include any embodiment described above in combination with another other embodiments described above.

It should be appreciated that the above teachings, concepts, or aspects from the pregnancy monitoring system 100a can be incorporated with any embodiment described above or the pregnancy monitoring system 100a can include any embodiment described above in combination with another other embodiments described above. For example, any of the various functionalities or determinations performed by the controller 110 in the pregnancy monitoring system 100a may be performed by the controller of any of the embodiments disclosed herein. As another example, the control electrical circuitry of the controller 110 can be configured to determine the direction of the internal and/or external source loads and can be further configured to detect and/or monitor motion of the pregnant subject 10 and/or of the fetus. Moreover, the controller 110 can generate and/or display any output or combinations thereof, as described herein. For example, the controller 110 can generate and/or display output related to the internal and/or external source loads and output related to the motion of the pregnant subject 10 and/or of the fetus.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In an embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

Additionally, as will be appreciated by one of ordinary skill in the art, principles of the present disclosure, including components, may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create a means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

In an embodiment, a pregnancy monitoring system disclosed herein can be integrated in such a manner that the pregnancy monitoring operates as a unique system configured specifically for the function of determining the external source loads, internal source loads, motion of the pregnant subject, motion of the fetus inside the pregnant subject, output related to the foregoing, combinations thereof, and the like, and any associated computing devices of the pregnancy monitoring system operate as specific use computers for purposes of the claimed system, and not general use computers. In an embodiment, at least one associated computing device of the pregnancy monitoring system operates as a specific use computer for purposes of the claimed system, and not general use computers. In an embodiment, at least one of the associated computing devices of the pregnancy monitoring system is hardwired with a specific ROM to instruct the at least one computing device. In an embodiment, one of ordinary skill in the art recognizes that the pregnancy monitoring system effects an improvement at least in the technological field of pregnancy monitoring systems.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A system for monitoring a pregnant subject, the system comprising:
    one or more sensors configured to generate one or more signals related to an internal source load and an external source load received by the pregnant subject; and
    a controller including control electrical circuitry operably coupled to the one or more sensors and configured to receive the one or more signals therefrom, the control electrical circuitry configured to:
        perform a comparison of the internal source load to the external source load; and
        generate an output related to the comparison of the internal source load to the external source load at least partially based on the one or more signals received from the one or more sensors.

2. The system of claim 1, wherein at least one signal of the one or more signals related to the internal source load is generated at a different time from at least one signal of the one or more signals related to the external source load.

3. The system of claim 1, wherein the output from the controller is related to one or more of a position of the fetus in the pregnant subject, motion of the fetus, or an orientation of the fetus in the pregnant subject.

4. The system of claim 3, wherein the controller includes memory configured to store data that is generated at least partially from the control electrical circuitry and that is related to one or more of the position of the fetus in the pregnant subject, the motion of the fetus, or the orientation of the fetus.

5. The system of claim 1, wherein the control electrical circuitry of the controller is configured to receive information related to the external source load.

6. The system of claim 5, wherein the control electrical circuitry of the controller is configured to distinguish the external source load from the internal source load.

7. The system of claim 6, wherein:
    the one or more sensors include a first sensor positionable at a first distance relative to an outer surface of skin of the pregnant subject and a second sensor positionable at a second distance relative to the outer surface of the skin of the pregnant subject that is greater than the first distance; and
    the control electrical circuitry of the controller is configured to distinguish the internal source load from the external source load at least partially based on one or more of a difference in time between the respective sensing signals received from the first sensor and the second sensor or a difference in strength between the respective sensing signals received from the first sensor and the second sensor.

8. The system of claim 7, further including an attenuating material positioned between the first sensor and the second sensor.

9. The system of claim 6, wherein:
    the one or more sensors include a first sensor positionable at a first location relative to a reference location on the pregnant subject and a second sensor positionable at a second location relative to the reference location on the pregnant subject that is different from the first location; and
    the control electrical circuitry of the controller is configured to distinguish between the internal source load and the external source load based at least partially on one or more of a difference in time between the respective sensing signals received from the first sensor and the second sensor or a difference in strength between the respective sensing signals received from the first sensor and the second sensor.

10. The system of claim 1, wherein the received information that is related to the external source load is received from the pregnant subject, and the control electrical circuitry of the controller is configured to compare the received information that is related to the external source load, which is received from the pregnant subject, to the external source load that is determined at least partially based on the one or more signals received from the one or more sensors.

11. The system of claim 1, wherein the control electrical circuitry of the controller is configured to receive information related to one or more of a position of a fetus in the pregnant subject, a motion of the fetus, or an orientation of the fetus.

12. The system of claim 1, wherein the one or more sensors include a first sensor configured to generate one or more first signals related to at least one of the internal source load or the external source load, and a second sensor configured to generate one or more second signals related to one or more of an orientation, a position, or motion of a fetus in the pregnant subject.

13. The system of claim 1, wherein the control electrical circuitry of the controller is configured to correlate the external source load with one or more of a position of a fetus in the pregnant subject, a motion of the fetus, or an orientation of the fetus.

14. The system of claim 13, wherein the control electrical circuitry of the controller is configured to determine a force imparted on at least one portion of the fetus.

15. The system of claim 13, wherein the control electrical circuitry of the controller is configured to determine a proximity between a position of the external source load received by the pregnant subject and a position of a portion of the fetus.

16. The system of claim 13, wherein the control electrical circuitry of the controller is configured to substantially continuously determine one or more of the position of the fetus, motion of the fetus, or the orientation of the fetus.

17. The system of claim 1, wherein the controller includes memory configured to store data related to the one or more signals received from the one or more sensors.

18. The system of claim 17, wherein the data includes one or more of a date, a time, or a magnitude associated with at least one of the one or more signals received from the one or more sensors.

19. The system of claim 1, further including a personal electronic device having a display, wherein the controller is configured to display the output from the controller on the display of the personal electronic device.

20. The system of claim 1, wherein the controller is configured to transmit the output from the controller to an electronic device.

21. The system of claim 20, wherein the output includes one or more recommendations related to one or more of a health of the pregnant subject or a health of a fetus in the pregnant subject.

22. The system of claim 20, wherein the electronic device is configured to display one or more recommendations related to one or more of a health of the pregnant subject or a health of a fetus in the pregnant subject, the one or more recommendations being based at least partially on the output received from the controller at the electronic device.

23. The system of claim 1, further including a garment wearable by the pregnant subject, the garment including at least one of the one or more sensors.

24. The system of claim 1, wherein the one or more sensors include a first sensor configured to emit a first signal detectable by a second sensor, and the second sensor configured to emit a second signal detectable by the first sensor.

25. The system of claim 24, wherein the control electrical circuitry of the controller is configured to determine a position of the first sensor relative to the second sensor at least partially based on one or more of the first signal or the second signal.

26. A wearable system for monitoring a pregnant subject, the wearable system comprising:
one or more wearable elements sized and configured to be worn by the pregnant subject;
one or more sensors configured to generate one or more signals related to an internal source load and an external source load received by the pregnant subject, at least one of the one or more sensors carried by the one or more wearable elements; and
a controller including control electrical circuitry operably coupled to the one or more sensors and configured to receive the one or more signals therefrom, the control electrical circuitry configured to:
perform a comparison of the internal source load to the external source load; and
generate an output related to the comparison of the internal source load to the external source load at least partially based on the one or more signals received from the one or more sensors.

27. The wearable system of claim 26, wherein the one or more wearable elements include fabric sized and configured to at least partially wrap about an abdomen of the pregnant subject.

28. The wearable system of claim 26, wherein at least one of the one or more wearable elements includes an adhesive configured to removably attach the at least one of the one or more wearable elements together with at least of the one or more sensors to the pregnant subject.

29. The wearable system of claim 26, wherein the control electrical circuitry of the controller is configured to distinguish between the internal source load and the external source load.

30. The wearable system of claim 29, wherein:
the one or more sensors include a first sensor positionable at a first distance relative to an outer surface of skin of the pregnant subject and a second sensor positionable at a second distance relative to the outer surface of the skin of the pregnant subject that is greater than the first distance; and
the control electrical circuitry of the controller is configured to distinguish between the internal source load and the external source load based at least partially on a difference in time between the respective sensing signals received from the first sensor and the second sensor or a difference in strength between the respective sensing signals received from the first sensor and the second sensor.

31. The wearable system of claim 29, wherein:
the one or more sensors include a first sensor positionable at a first location relative to a reference location on the pregnant subject and a second sensor a second location relative to the reference location on the pregnant subject that is different from the first location; and
the control electrical circuitry of the controller is configured to distinguish between the internal source load and the external source load based at least partially on a time difference between the respective sensing signals received from the first sensor and the second sensor or a difference in strength between the respective sensing signals received from the first sensor and the second sensor.

32. The wearable system of claim 31, further including an attenuating material positioned between and attached to the first sensor and the second sensor.

33. The wearable system of claim 26, wherein the one or more sensors define a sensor array configured to be distributed about an abdomen of the pregnant subject.

34. The wearable system of claim 26, wherein the one or more sensors include a first sensor configured to detect the external source load received by the pregnant subject, and a second sensor configured to generate one or more signals related to the internal source load resulting from motion of a fetus inside the pregnant subject.

35. The wearable system of claim 26, wherein the one or more signals are related to one or more of a position or an orientation of a fetus inside the pregnant subject.

36. The wearable system of claim 35, wherein the controller includes memory configured to store data related to the one or more signals received from the one or more sensors.

37. The wearable system of claim 36, wherein the data includes one or more of a date, a time, or a magnitude associated with at least one of the one or more signals received from the one or more sensors.

38. The wearable system of claim 26, wherein the control electrical circuitry of the controller is configured to receive input related to the one or more of a position of a fetus in the pregnant subject, an orientation of the fetus, or a size of the fetus, the input being based at least partially on an entry received from a user.

39. The wearable system of claim 26, wherein the controller is configured to generate an alert when one or more of the internal source load or the external source load exceed a threshold load.

40. The wearable system of claim 26, wherein the control electrical circuitry of the controller is configured to correlate one or more of the internal source load with one or more of a position of a fetus in the pregnant subject or an orientation of the fetus.

41. The wearable system of claim 26, further including a personal electronic device having a display, wherein the controller is configured to display the output from the controller on the display of the personal electronic device.

42. The wearable system of claim 26, wherein the controller is configured to transmit the output from the controller to an electronic device, wherein the output includes one or more recommendations related to one or more of a health of the pregnant subject or a health of a fetus in the pregnant subject.

43. The wearable system of claim 26, further including one or more load-sensitive elements configured to generate an alert when one or more of the internal source load or the external source load exceed a threshold load.

44. A method of monitoring a pregnant subject, the method comprising:
at a controller, receiving one or more signals from one or more sensors that detect one or more forces associated with an internal source load and an external source load received by the pregnant subject;
at the controller, determining the internal source load and the external source load based at least partially on the one or more signals received from the one or more sensors;
at the controller, performing a comparison of the internal source load to the external source load; and
generating an output related to the comparison of the external source load to the internal source load.

45. The method of claim 44, further including distinguishing the external source load from the internal source load by processing the one or more signals with the controller.

46. The method of claim 44, wherein:
the one or more sensors include a first sensor positioned at a first distance relative to an outer surface of skin of the pregnant subject and a second sensor positioned at a second distance relative to the outer surface of the skin of the pregnant subject that is greater than the first distance; and
the control electrical circuitry of the controller is configured to distinguish the internal source load from the external source load at least partially based on one or more of a difference in time between the respective sensing signals received from the first sensor and the second sensor or a difference in strength between the respective sensing signals received from the first sensor and the second sensor.

* * * * *

UNITED STATES PATENT AND TRADEMARK OFFICE
CERTIFICATE OF CORRECTION

PATENT NO. : 10,165,975 B2
APPLICATION NO. : 14/936828
DATED : January 1, 2019
INVENTOR(S) : Roderick A. Hyde et al.

It is certified that error appears in the above-identified patent and that said Letters Patent is hereby corrected as shown below:

In the Claims

Column 28, Claim 28, Line 36, delete "together with at least of the one or" and insert -- together with at least one of the one or -- therefor.

Column 28, Claim 31, Line 60, delete "and a second sensor a second location" and insert -- and a second sensor positionable at a second location -- therefor.

Signed and Sealed this
Thirteenth Day of August, 2019

Andrei Iancu
*Director of the United States Patent and Trademark Office*